US010960191B2

(12) United States Patent
Cinquin et al.

(10) Patent No.: US 10,960,191 B2
(45) Date of Patent: Mar. 30, 2021

(54) IMPLANTABLE INTESTINAL REACTOR (71) Applicants: UNIVERSITE GRENOBLE ALPES, Saint Martin d'Heres (FR); CENTRE HOSPITALIER UNIVERSITAIRE GRENOBLE, La Tronche (FR)

(72) Inventors: Philippe Cinquin, Saint Nazaires les Eymes (FR); Dominique Schneider, Saint Martin d'Heres (FR); Max Maurin, Meylan (FR); Donald Martin, Gieres (FR); Sarra El Ichi, La Tour du Pin (FR); Abdelkader Zebda, Grenoble (FR); Jean-Pierre Alcaraz, Pontcharra (FR); Fabian Reche, Sainte Agnes (FR); Patrick Tuvignon, Albi (FR); Jacques Thelu, Crolles (FR); Audrey Le Gouellec, Uriage (FR); Bertrand Toussaint, Saint Egreve (FR)

(73) Assignees: UNIVERSITE GRENOBLE ALPES, Saint Martin d'Heres (FR); CENTRE HOSPITALIER UNIVERSITAIRE GRENOBLE, La Tronche (FR)

( * ) Notice: Subject to any disclaimer, the term of this patent is extended or adjusted under 35 U.S.C. 154(b) by 236 days.

(21) Appl. No.: 15/564,105

(22) PCT Filed: Apr. 4, 2016

(86) PCT No.: PCT/EP2016/057304
§ 371 (c)(1),
(2) Date: Oct. 3, 2017

(87) PCT Pub. No.: WO2016/156612
PCT Pub. Date: Oct. 6, 2016

(65) Prior Publication Data
US 2018/0078746 A1 Mar. 22, 2018

(30) Foreign Application Priority Data
Apr. 3, 2015 (FR) ...................... 15 2927

(51) Int. Cl.
*A61M 31/00* (2006.01)
*A61K 35/747* (2015.01)
*A61B 5/00* (2006.01)
*B01D 69/14* (2006.01)
*A61K 38/28* (2006.01)
*A61L 31/04* (2006.01)
*A61L 31/14* (2006.01)
*A61L 31/16* (2006.01)
*A61M 25/04* (2006.01)

(52) U.S. Cl.
CPC ......... *A61M 31/002* (2013.01); *A61B 5/6871* (2013.01); *A61B 5/6873* (2013.01); *A61K 35/747* (2013.01); *A61K 38/28* (2013.01); *A61L 31/042* (2013.01); *A61L 31/14* (2013.01); *A61L 31/146* (2013.01); *A61L 31/16* (2013.01); *B01D 69/144* (2013.01); *A61L 2300/43* (2013.01); *A61L 2400/18* (2013.01); *A61M 25/04* (2013.01); *A61M 2210/106* (2013.01); *A61M 2210/1053* (2013.01); *A61M 2210/1057* (2013.01); *Y02A 50/30* (2018.01)

(58) Field of Classification Search
CPC ............... A61M 31/002; A61M 25/04; A61M 2210/1053; A61M 2210/1057; A61M 2210/106; A61K 35/747; A61K 38/28; A61B 5/6873; A61B 5/6871; B01D 69/144; A61L 31/042; A61L 31/14; A61L 31/146; A61L 31/16; A61L 2300/43; A61L 2400/18; Y02A 50/30; A61P 3/04
See application file for complete search history.

(56) References Cited

U.S. PATENT DOCUMENTS

| 5,759,539 A | 6/1998 | Whitmire |
| 5,820,584 A | 10/1998 | Crabb et al. |

(Continued)

FOREIGN PATENT DOCUMENTS

| WO | WO-2004/087233 | 1/2006 |
| WO | WO-2007092390 | 8/2007 |

OTHER PUBLICATIONS

Bazian. Modified bacteria may be useful in treating diabetes. NHS Website. 2015;1-6.*
Preliminary Search Report for FR 1552927, dated Jan. 19, 2016.
International Search Report for PCT/EP2016/057304, dated Jun. 20, 2016.
Fishman, et al., "A novel endoscopic delivery system for placement of a duodenal-jejunal implant for the treatment of obesity and type 2 diabetes", 2008, Abstract only, Conf Proc IEEE Eng Med Biol Soc.

(Continued)

*Primary Examiner* — Lynn Y Fan
(74) *Attorney, Agent, or Firm* — B. Aaron Schulman, Esq.; Stites & Harbison, PLLC (57) ABSTRACT

The device, that can be implanted in the intestinal cavity, comprises a reactor comprising a semi-permeable or porous membrane or coating linked to a element for attachment to an intestinal or gastric wall. The reactor can be in the form of a ribbon, a structure having more than two faces or an open structure delimiting a lumen, comprising, or formed from, a semi-permeable or porous membrane. The reactor can also delimit, at least partially with the semi-permeable or porous membrane of same, a closed inner space. The reactor can comprise or carry enzymes or micro-organisms, in particular bacteria or yeast. The reactor is used for generating a chemical reaction with one or more molecules present in the intestine, or for producing one or more biologically active molecules. It can, in particular, be used for consuming sugars, disaccharides and simple sugars or producing essential amino acids or other molecules having a positive effect on the health.

21 Claims, 2 Drawing Sheets

(56) References Cited

U.S. PATENT DOCUMENTS

| | | | |
|---|---|---|---|
| 7,025,791 B2 | 4/2006 | Levine et al. |
| 7,122,058 B2 | 10/2006 | Levine et al. |
| 7,267,694 B2 | 9/2007 | Levine et al. |
| 7,320,788 B2 | 1/2008 | Shan et al. |
| 7,329,285 B2 | 2/2008 | Levine et al. |
| 7,347,875 B2 | 3/2008 | Levine et al. |
| 7,476,256 B2 | 1/2009 | Meade et al. |
| 7,608,114 B2 | 10/2009 | Levine et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,771,382 B2 | 8/2010 | Levine et al. |
| 7,771,463 B2 * | 8/2010 | Ton | A61F 2/88 623/1.11 |
| 7,815,589 B2 | 10/2010 | Meade et al. |
| 7,815,591 B2 | 10/2010 | Levine et al. |
| 7,819,836 B2 | 10/2010 | Levine et al. |
| 7,837,643 B2 | 11/2010 | Levine et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,096,966 B2 | 1/2012 | Levine et al. |
| 8,137,301 B2 | 3/2012 | Levine et al. |
| 8,148,105 B2 | 4/2012 | Vora et al. |
| 8,162,871 B2 | 4/2012 | Levine et al. |
| 8,303,669 B2 | 11/2012 | Meade et al. |
| 8,425,451 B2 | 4/2013 | Levine et al. |
| 8,486,153 B2 | 7/2013 | Levine et al. |
| 8,628,583 B2 | 1/2014 | Meade et al. |
| 8,771,219 B2 | 7/2014 | Meade et al. |
| 8,801,647 B2 | 8/2014 | Melanson et al. |
| 8,834,405 B2 | 9/2014 | Meade et al. |
| 8,834,553 B2 | 9/2014 | Melanson et al. |
| 8,870,806 B2 | 10/2014 | Levine et al. |
| 8,882,698 B2 | 11/2014 | Levine et al. |
| 8,920,358 B2 | 12/2014 | Levine et al. |
| 8,980,257 B2 | 3/2015 | Siegel et al. |
| 9,017,667 B2 | 4/2015 | Berner |
| 9,084,669 B2 | 7/2015 | Meade et al. |
| 9,095,416 B2 | 8/2015 | Meade et al. |
| 9,155,609 B2 | 10/2015 | Levine et al. |
| 9,237,944 B2 | 1/2016 | Meade et al. |
| 9,265,596 B2 | 2/2016 | Shank et al. |
| 9,278,020 B2 | 3/2016 | Levine et al. |
| 9,585,783 B2 | 3/2017 | Meade et al. |
| 9,597,215 B2 | 3/2017 | Chamorro, III et al. |
| 9,636,245 B2 | 5/2017 | Chamorro, III et al. |
| 9,642,734 B2 | 5/2017 | Melanson et al. |
| 2002/0103522 A1 | 8/2002 | Swoyer et al. |
| 2004/0062809 A1 | 4/2004 | Honiger et al. |
| 2004/0213825 A1 * | 10/2004 | Levy | A61K 9/0053 424/423 |
| 2004/0249362 A1 * | 12/2004 | Levine | A61F 5/0076 604/523 |
| 2005/0249719 A1 | 11/2005 | Shan et al. |
| 2009/0035351 A1 | 2/2009 | Berglund et al. |
| 2010/0063518 A1 | 3/2010 | Baker et al. |
| 2010/0092451 A1 | 4/2010 | Gass et al. |
| 2010/0196955 A1 | 8/2010 | Vora et al. |
| 2011/0171201 A1 | 7/2011 | Siegel et al. |
| 2011/0236369 A1 | 9/2011 | Berner |
| 2011/0250510 A1 | 10/2011 | Cinquin et al. |
| 2015/0184146 A1 | 7/2015 | Siegel et al. |
| 2016/0235825 A1 | 8/2016 | Siegel et al. |
| 2017/0081626 A1 | 3/2017 | El Ichi et al. |

OTHER PUBLICATIONS

Gersin, et al., "Duodenal-jejunal bypass sleeve: a total endoscopic device for the treatment of morbid obesity", 2007, Abstract Only, Surg Innov.

* cited by examiner

IMPLANTABLE INTESTINAL REACTOR

The present invention relates to a device making it possible to carry out conversion or synthesis reactions within the intestine, and its use to treat a pathology, correct a deregulation or prevent the appearance of a pathology or deregulation.

Glucose is the typical example of the molecule whose intestinal absorption one may wish to reduce, for example in the case of excess weight or type II, or even type I, diabetes.

Many proposals have been made to allow enzymes or microorganisms to reach the intestine without being broken down by the gastric passage. Examples include Lactaid®, a dietary supplement based on galactosidase, in particular alpha-galactosidase and beta-galactosidase, intended to treat lactose intolerance related to a deficit of this enzyme. More generally, there are various food supplements containing bacteria, such as the bidifus bacteria. The effectiveness of these approaches is, however, greatly diminished by the fact that these products are altered in the small intestine by an aggressive environment, in particular for proteins, and by the fact that the active components do not stay long in the duodenum and the jejunum, areas where the carbohydrate concentrations, and more generally concentrations in various nutrients, are maximal.

The present invention therefore aims to propose a device making it possible to make active products bioavailable in the intestine, resolving the problems of the prior art.

Another aim of the invention is to propose such a device that allows bioavailability over a controllable length of time, which may be more or less long.

Still another aim of the invention is to propose such a device that makes it possible to make a wide variety of active products bioavailable, ranging from enzyme-type molecules and possible any cofactor to a microorganism or a cellular mass.

The invention therefore relates to a device implantable in the intestinal cavity. This device comprises a reactor positionable in the intestinal cavity. Implantable means that the device and its reactor are kept in place in the intestinal cavity. Positionable means that the reactor is kept in the location where it is initially positioned. The reactor keeps itself in this position for the usage duration, which may reach several days, weeks, months or years. The reactor may advantageously be implanted orally, then removed the same way, for example by endoscopy. It is kept in place owing to a maintaining or fastening element, for example an anchoring part in the intestinal or gastric wall or a gastric or intestinal stent, as will be outlined later.

The reactor comprises a biocompatible material, preferably a biocompatible polymer material, which is able to immobilize or contain an active element or product. This material may be in the form of a membrane, a sheet, a mass of material or a coating. An active product refers to a product able to generate a chemical or biological reaction with one or more molecules present in the intestine or to produce one or more potentially interesting molecules for the aim sought by the invention. Below, we will outline the types of active products and their applications, but the notion of active product includes both chemical molecules and living microorganisms.

By definition, a reactor may on the one hand be an element that contains an active product (placed in this element beforehand) while allowing it to interact with the intestinal environment either by releasing at least one active product or by reacting with one of the elements contained in the intestinal environment coming into contact with the content of the reactor. A reactor may on the other hand be a support for an active product which, attached to the support, will interact with the intestinal environment either by releasing at least one active product or by reacting with one or more elements contained in the intestinal environment. The reactor can therefore be defined as containing or supporting an active product, which for example precludes an open tube in which a liquid product flows.

The reactor may comprise a membrane, a sheet, a material or material mass, or a coating having an appropriate permeability. It may, but does not exclusively, involve a semipermeable material. The material or material mass intended to serve as support for the active product or element may assume any form, for example ribbon, tube, structure comprising more than two faces, etc.

In a first embodiment, the reactor may be a device made from a biocompatible material defining, at least in part with its semipermeable or porous membrane, a closed inner space, in which the active product can be placed. The device then includes at least one outer surface defined by a semipermeable or porous membrane made from a biocompatible material, preferably a biocompatible polymeric material. The device may include an inner structure, such as a frame with a suitable rigidity, giving the reactor its shape. It may also not include such a structure and be completely flexible, for example a closed elongate tube or bag.

The reactor preferably has an elongated shape. Its length may in particular be comprised between about 1 cm and about 100 cm, in particular between about 1 cm and about 50 cm, in particular between about 1 cm and about 20 cm, preferably between about 2 cm and about 10 cm. Its greater width or its diameter may in particular be comprised between about 0.5 cm and about 3 cm, preferably between about 1 cm and about 2 cm. The thickness of the material or the membrane may be comprised between about 0.5 mm and about 2 mm, for example about 1 mm. The inner space of the reactor may in particular be comprised between about 1 mL and about 180 mL, preferably between about 2 mL and about 50 mL.

The reactor may be in the form a network of an elongate bag or a cylindrical, semi-cylindrical or substantially flat tube. It may also be in the form of tubules, or even of fibers. Its structure is advantageously flexible.

Preferably, the entire surface or more than about 60, 70, 80 or 90% thereof is made up of the semipermeable or porous membrane.

The reactor may include several compartments, for example at least 2. In particular, the reactor may comprise, inside the space defined by the first membrane, a compartment, here called second compartment, defined by a second semipermeable or porous membrane, the properties of which, in particular the porosity, are different from the prior one.

The reactor may be fastened to a cord. The cord has a cross-section and material that do not harm the digestive system. Its cross-section may for example be round, semi-round or flat. The cord may be continuous (single-strand) or an assembly of threads or other elementary units, assembled to form the cord, for example in the form of a braid or a textile structure. The cord may be made from a biocompatible organic or inorganic material. It may be a synthetic polymer-based material (for example, polyethylene, e.g., Dacron®) or have a metal base (for example, nickel-titanium alloy). It has strength with respect to the acidity and enzymes present, as well as sufficient breaking strength to withstand forces applied on the reactor by intestinal transit.

The fastening of the reactor to the cord can be done in any known manner, for example by gluing, welding, sewing, knotting, or the fact that the cord is in a single piece with the reactor. In one embodiment, the cord is connected to the reactor by a swivel or the like, allowing one to rotate relative to the other.

In one embodiment, the cord is surrounded by cylindrical segments, the inner diameter of which is larger than the diameter of the cord such that these segments, called gyroplanes, can rotate around the cord and prevent the latter from twisting under the action of the mechanical stresses exerted on the device. The use of segments makes it possible to preserve the flexibility of the assembly. For example, segments from about 0.5 to about 5 cm, preferably about 1 to about 4 cm, e.g., about 3 cm, can be used.

At its end opposite its fastening point to the reactor, the cord can be connected to, or include in one piece, an anchoring part. What we call an anchoring part is a device or part of a device for anchoring in or on a tissue wall. Such devices will be described later. The cord has a length that makes it possible, taking into account the tissue fastening point, to position the reactor in the desired location in the intestine, in particular in the duodenum, preferably downstream from the mouth of the biliary duct. The cord or cord part may in particular have a length comprised between about 10 cm and about 50 cm, preferably between about 10 cm and about 40 cm, more particularly between about 15 cm and about 30 cm. The overall length of the reactor plus cord may therefore be comprised between about 11 cm and about 150 cm, in particular between about 11 cm and about 60 cm.

The active product can be present in the inner space of the reactor in free form or associated with a support or matrix. Preferably, the reactor contains a filler material or matrix, which may be particulate, granular or in the form of a unitary mass or block, optionally porous. The active product may simply be mixed with said material, particularly particulate or granular, or adsorbed or retained by weak bonds on its surface or associated another way known per se. The material, in particular when in the form of a mass, may be porous or stable or dissolvable under the conditions prevailing in the intestine. Example materials include chitosan, barium alginate, cellulose hydrogel, agar hydrogel or PVA (polyvinyl alcohol) hydrogel.

In a second embodiment, the reactor has at least two free faces (i.e., able to come into contact with the medium in which the reactor is submerged, i.e., the intestinal fluid). According to a first mode, this reactor has a flat geometry; it may assume the form of a ribbon (tape) or a structure having more than two faces. According to a second mode, the reactor is a tube with any cross-section, for example round, semi-round, parallelepiped, the aforementioned two faces therefore being formed by the outer face and the inner face.

Microorganisms can be immobilized, a biofilm can be formed and/or active molecules can be immobilized on at least one of the two faces of this reactor.

In the first mode, this reactor may be in the form of a smooth ribbon, optionally in the form of a helix. It may also have a structure in which the reactor has local irregularities making it possible to increase the exchange surface area relative to the apparent surface. It may also have a complex structure with L-shaped, T-shaped, star-shaped with 4, 5, 6 or more branches, etc., cross-sections, which makes it possible to multiply the surfaces on which the active product can be immobilized.

The reactor may be fastened to a cord, of the type defined above. The fastening of the reactor to the cord can be done in any known manner, for example by gluing, welding, sewing, knotting. A swivel or the like may be used. The cord may be equipped with gyroplane segments as mentioned above. The cord has a length that makes it possible, taking into account the tissue fastening point, to position the reactor in the desired location in the intestine, in particular in the duodenum, preferably downstream from the mouth of the biliary duct. The cord or cord part may in particular have a length making it possible to position the reactor correctly in light of the length thereof. The overall length of the reactor plus cord may in particular be comprised between about 1 cm and about 150 cm, in particular between about 1 cm and about 50 cm, preferably between about 10 cm and about 40 cm, more particularly between about 15 cm and about 30 cm. The length of the reactor may in particular be comprised between about 1 cm and about 100 cm, in particular between about 1 cm and about 50 cm, more particularly between about 10 cm and about 30 cm.

According to one particular mode, this cord may also be an extension of the reactor, i.e., in a single piece therewith, optionally with a smaller cross-section. A distinction is then made between the reactor part strictly speaking, which will immobilize the active product, and the so-called cord part, which is not intended to receive this active product. According to one alternative, the reactor, cord and anchoring part are in a single piece. This may for example be a ribbon. The length of the reactor may then typically be from about 10 to about 60 cm.

In the case of the first mode, the width of the faces (of the ribbon if applicable) may typically be comprised between about 0.5 cm and about 3 cm, preferably between about 1 cm and about 2 cm. The thickness of the material making up the reactor may be comprised between about 0.1 mm and about 2 mm, for example about 0.5 mm. The exchange surface may in particular vary from about 1 $cm^2$ to about 600 $cm^2$, for two faces. The active part of the reactor, i.e., the part of the reactor that will be the support for the active product, may be limited to a fraction of the reactor, situated opposite this anchoring point.

In the case of the second mode, the exchange surface of the reactor may be comprised between about 5 $cm^2$ and about 1800 $cm^2$, in particular between about 10 $cm^2$ and about 900 $cm^2$, preferably between about 100 $cm^2$ and about 300 $cm^2$.

At its end opposite its fastening point to the reactor, the cord can be connected to, or include in one piece, an anchoring part. What we call an anchoring part is a device or part of a device for anchoring in or on a tissue wall.

In general, the ribbon can be kept in place in several ways: either by fastening it to a nasogastric probe, or to a gastrostomy probe, or by an endoscopic clip at the gastric antrum, depending on the anticipated usage duration of the reactor or the pathologies of the patient that justify placing a gastrostomy.

Alternatively, in place of a ribbon, one or several parts are used centered on the cord, preferably on a gyroplane segment as described above. The part has an essentially cylindrical shape or cross-section, but which is irregular so as to prevent a laminar flow in contact with the part, this surface irregularity being able to be obtained by thickness or diameter variations, in the longitudinal and/or diametrical direction of the cylindrical shape, and/or by the presence of cavities set back from the cylindrical shape and/or protuberances extending past the cylindrical shape. One appropriate example is a helical shape or a twist segment (twisted shape) similar to so-called twisted columns, with the outer edges sharp or rounded. These parts fit into a cylinder whose diameter may for example be comprised between about 3 and about 30 mm, preferably between about 5 and about 10 mm.

For the various embodiments, the reactor or part of the reactor (the membrane) can be made from a biocompatible polymeric material, in particular the semi-permeable or porous membrane, the ribbon or other parts may be made from a natural or synthetic polymeric material withstanding the environment in the intestine, in particular the pH condition and enzymes present, particularly enzymes present in the intestinal environment where the reactor is placed, particularly pancreatic and biliary enzymes, as well as the enzymes produced by the intestinal flora, in particular proteases. In particular, the polymer may be chitosan or another biocompatible polymer, for example: polyvinyl alcohol, polymethyl methacrylate, polyacrylonitrile and sodium methanesulfonate copolymer, or PAN-methallyl sulfonate, for example membrane AN69 (WO 2002-000775); copolymers such as chitosan-polyethylene glycol; cellulose polymer, e.g., cellulose acetate. Preferably, the polymer, e.g., chitosan, has a sufficient degree of cross-linking to withstand the environment in the intestine. It may also be made resistant to the acidic pH or acids by one or several appropriate additives. According to one embodiment, the chitosan is implemented with a cross-linking agent, for example genipin, and/or with an additive making it possible to improve the resistance of the membrane to acids, for example cafeic acid.

Alternatively, the reactor or part of the reactor (the membrane) can be formed by a composite structure, with a support and a coating made from a synthetic or natural biocompatible polymer. The support may in particular be a textile material, woven or nonwoven, impregnated and/or coated with a polymeric material as described above.

Alternatively, the reactor or part of the reactor (the membrane) can be formed by a textile structure with a base of synthetic polymer (for example, polyester, such as Dacron®), or a metal base (for example, nickel-titanium alloy).

The thickness of the material or the membrane may be comprised between about 0.1 mm and about 2 mm, for example about 1 mm.

The pores in the material or the membrane may have variable diameter, depending on what they are intended to allow to pass or to stop. In general, the diameter of the pores may be between 0.1 nm and 500 nm. Between 0.1 nm and 5 nm, preferably between 0.5 nm and 2 nm, the pores allow substances to pass such as sugars and active molecules, and in particular retain the enzymes and microorganisms. It is also possible to adjust the diameter of the pores when manufacturing the material, for example by modifying: the concentration of the polymer, e.g., chitosan, in the solvent (e.g., acetic acid for chitosan), the chitosan/cross-linking agent ratio, the molecular weight of the polymer, e.g., chitosan, before dissolution and shaping of the membrane. It is also possible to glue commercially-available semi-permeable membranes (for example made from cellulose acetate or AN69, etc.), the degree of porosity of which can be chosen from a wide range, to the surface of the reactor. In one alternative, these commercially-available membranes may be covered with a layer of the polymers described in the invention (for example, chitosan modified by adding cross-linking agents) to improve the resistance to the physico-chemical conditions of the intestine and to retain their semi-permeability properties longer.

In the case of the reactor including at least 2 compartments, the porosity of the two semi-permeable or porous membranes can be different.

In one embodiment, the material or the membrane includes pores that do not allow the proteases to pass. In particular, such a membrane is used for a hollow reactor intended to contain enzymes that must be protected from the proteases present in the intestinal fluid, without preventing the substrate of these enzymes from penetrating the inside of the reactor.

A chitosan-based porous membrane may be prepared using a method comprising the following steps: prepare a solution in a ratio of 5 to 15 (in mg), of chitosan to 0.75 to 1.25 (in mL) of acetic acid diluted at 0.4 to 0.6 vol % in water; agitate for 2 hours; add a cross-linking agent, for example genipin, in particular from 0.002 to 0.005 wt % by volume of genipin; cafeic acid, in particular from 0.001 to 0.005 wt % by volume of cafeic acid; agitate for 30 minutes; pour on an anti-adhesive substrate; dry slowly, in particular for 2 to 4 days at ambient temperature.

For the different embodiments, the cord or cord part has a length that makes it possible, taking into account the tissue fastening point, to position the reactor in the desired location in the intestine, in particular in the duodenum, preferably downstream from the mouth of the biliary duct. The cord or cord part may in particular have a length comprised between about 10 cm and about 20 cm, in particular between about 10 cm and about 15 cm.

The anchoring part of the device can be attached to the tissue wall (for example, wall of the stomach), by any fastening means known by those skilled in the art, for example link, clip or staple. The fastening of the cord to the anchoring part, when these parts are not in a single piece, can be done in any known manner, for example by gluing, welding, sewing, knotting.

In one particular embodiment, the anchoring part is a pyloric stent, which is fixed in the gastric antrum, just upstream from the pylorus. This may in particular involve a stent whose structure is deployed to be immobilized in the gastric antrum upstream from the pylorus, like in the case of the stent of the Endobarrier® device.

According to another embodiment, the reactor comprises at least one part, a block or mass made from biocompatible material, attached to the cord. In one particular mode, the reactor includes a multi-part cord, for example from 2 to 20 parts, attached to one another by the cord. Advantageously, each part is contained in a structure attached to the cord, for example a net or the like, for example made from polyester, e.g., Dacron®. These parts can be formed by compressing biocompatible polymeric material, optionally associated with various ingredients promoting shaping. Example polymeric materials to form the parts include chitosan and barium alginate. According to one particular mode, the enzyme(s) of interest are mixed with the polymeric material, e.g., chitosan. It is possible to make this mixture, then shape the mixture, for example by compression. Reference may be made to the manufacturing method described in French patent application no. 1,452,534 filed on Mar. 25, 2014.

A similar material can be used to form the aforementioned material parts, centered on the cord, such as cross-linked and expanded polyvinyl alcohol, in amorphous, crystalline or composite state, the materials from the group of biocompatible polyamines or polyesters, such as polyvinyl alcohol and polyacrylic acid polyester. These polymeric materials are able to have variable chain lengths, various branched and cross-linked structures and in the form of copolymers with different formulations giving the final material a structure and porosity chosen for the function to be performed. The hydrophilic or hydrophobic nature of this material conditions the durable bond of the enzymatic proteins, protein effectors or microbiota by affinity and adsorption. Chemical radicals can also be used to strengthen these bonds by strong covalent bonds.

According to another embodiment, the implantable reactor is an intestinal or digestive stent that can be coated in whole or in part with a biocompatible material, preferably a biocompatible polymeric material, or that can include a part formed from such a biocompatible material, for example a textile braid or structure, optionally coated with a polymeric material according to the invention. Said material can immobilize the active product or allow the development of a biofilm. Preferably, the stent is of the tubular type formed from a lattice that is deployed to marry the inside of the intestine. This stent can be dimensioned for placement in the duodenum, the small intestine or the colon.

The biocompatible material is preferably a polymer, as described with respect to the previous embodiment. In particular, the polymer may be chitosan or another biocompatible polymer, for example: polyvinyl alcohol, polymethyl methacrylate, or copolymers such as chitosan-polyethylene glycol or a mixture of these polymers. Preferably, the polymer, e.g., chitosan, has a sufficient degree of cross-linking to withstand the environment in the intestine. According to one embodiment, the chitosan is for example implemented with genipin and cafeic acid.

It may also involve a textile structure, in particular braid, from a synthetic polymer (for example, polyester, e.g., Dacron®) or have a metal base (for example, nickel-titanium alloy), in particular coated with a polymer as described supra.

By definition, in one embodiment, the device according to the invention may comprise the reactor, the cord or cord part and the anchoring part.

The invention not only relates to the raw reactor as described above, but also the reactor including the active ingredient. The active ingredient is inside the inner space of the reactor, with or without filler material or matrix, and/or on its surface, depending on the type of reactor.

The active product may in particular be chosen from among enzymes, microorganisms such as bacteria or yeasts, or eukaryotic cellular masses, in particular bacteria capable of digesting oligosaccharides.

The enzymes can particular be used with a reactor including an inner space in which the enzyme can be contained, with or without the presence of a filler material or other matrix, or mixed with a material such as chitosan to form a structure as previously described. As enzymes, it is in particular possible to use disaccharidases and/or enzymes that convert "simple" sugars, in particular those derived from the action of the disaccharidases on the disaccharides. Preferably, the two types of enzymes are combined. Among disaccharidases, examples in particular include lactase, maltase and beta-fructosidases, alpha-glucosidase, beta-glucosidase, beta-galactosidase, alone or in mixtures. As enzymes converting the simple sugars, examples include, alone or in mixture, glucose oxidase and glucose dehydrogenase, optionally combined with aldose reductase.

Glucose consumption before intestinal absorption is one very interesting embodiment. Disaccharidases are preferably provided, since the carbohydrates after the intestine preferably assume the form of disaccharides, and an enzyme making it possible to convert the simple sugars derived from the action of the previous enzyme. The glucose oxidase converts the glucose into gluconate and constitutes a first form. This will not be absorbed as well as glucose by the intestine, since the intestinal membranes do not have specific carriers for gluconate, whereas several transmembrane proteins are dedicated to carrying glucose. Furthermore, once absorbed by the body, a large majority of the gluconate is excreted directly by the kidneys. Enzymes such as glucose dehydrogenase, which need a cofactor, constitute a second form, since it is necessary to provide regeneration of the cofactor. For example, glucose dehydrogenase also produces gluconate, but it uses NAD+ (nicotinamide adenine dinucleotide) or NADP+ as electronic acceptor, and not oxygen. In this case, to regenerate the NADP+, it is possible to provide the presence of aldose reductase, capable of reducing the glucose into sorbitol. Yet sorbitol is only slightly absorbed by the intestine, since it is also used to treat obesity (with no noteworthy side effects at less than 17 g/kg/24 h), since it favors intestinal transit. In light of the fact that the about 10 L of chyme that leaves the stomach daily contains about 20 g·L−1 of carbohydrates, to eliminate about 200 mmol of glucose in 24 hours (or about 38 g, or about 8%, of the calorific ratio), an enzymatic activity is provided of about 140 UI. Thus, the reactor according to the invention may comprise aldose reductase, in particular in combination with glucose dehydrogenase.

In one particular embodiment of the invention, the reactor comprises at least 2 compartments. In the first is a first enzyme, for example a disaccharidase and optionally a cofactor, and in the other a second enzyme, for example an enzyme converting simple sugars, and optionally a cofactor. The cutoff thresholds of the membranes are adapted to avoid leaks of the enzymes and cofactors that the compartments contain while allowing the substrates to pass. Thus, a first compartment contains one or several disaccharidases (e.g., lactase, maltase, beta-fructosidase, alpha-glucosidase, beta-glucosidase, beta-galactosidase) and the membrane has a cutoff threshold (for example about 500 or 1000 g/mole) allowing the disaccharides to pass into this compartment, where they are converted into simple sugars, in particular glucose; the second compartment contains $NAD^+$ or $NADP^+$ and one or several enzymes converting the simple sugars (e.g., glucose oxidase and/or glucose dehydrogenase); it is separated from the first by a membrane having a cutoff threshold (for example, about 300 g/mole) making it possible to retain its content and to allow the simple sugars to pass that are formed in the first compartment.

According to the invention, the reactor may comprise enzymes such as lactase or other galactosidases, able to treat lactose intolerance, or glutenases, in particular cystine endoprotease or enzymes ALV001, ALV002 and ALV003, described in patent applications WO 2005-107786, WO 2008-115428, WO 2008-115411, WO 2010-021752, WO 2010-42203, to treat gluten intolerance.

The enzymes and the microorganisms can also play a role in the oriented development of the microbiota. For example, the action of the glucose oxidase has the interest of consuming oxygen and producing protons. Combined with the catalase (which disproportionates the produced $H_2O_2$ and prevents the potentially harmful action of $H_2O_2$ on the intestinal wall), glucose oxidase requires 1 mmol of $O_2$ to oxidize 2 mmol of glucose and allows consumption of the oxygen. The removal of a significant quantity of oxygen will exert a high selection pressure on the microbiota, in favor of anaerobic bacteria. Likewise, proton production will favor a acidophilic bacteria. Thus, the reactor according to the invention may comprise catalase, in particular in combination with glucose oxidase.

Protons can be produced, for example during the transformation of glucose into gluconate, or by the action of certain bacteria (*Lactobacillus acidophilus*, in particular) on the nutrients present in the intestinal lumen. Ammonium ions can be produced, for example by the action of the urease on the urea. Thus, the reactor according to the invention may comprise urease or any enzyme useful to influence the microbiota or the intestinal fluid, optionally in combination with glucose oxidase and/or glucose dehydrogenase. The chemical reactions can therefore be oriented to modify the pH of the digestive tube locally. These modifications will modify the composition of the microbiota. Yet the microbiota interacts with many physiological organs and systems. It is suspected of being involved in pathologies as varied as obesity, diabetes, hypercholesterolemia, certain cancers, Alzheimer's disease, etc. Coupling intervention on the microbiota through the modification of parameters such as the pH and the observation of clinical or biological parameters may therefore obtain the desired therapeutic effect for a given patient.

The reactor may allow the in situ production of digestive enzyme inhibitors and/or molecules, such as dimethyl-butanol, which reduces the TMA-oxide, or hormones, in particular stimulating satiety. To that end, the reactor may contain natural bacteria selected for the desired functions, or bacteria genetically modified to perform these functions of producing molecules of interest.

The bacteria may either be placed in the inner space of the reactor, or applied to its surface, depending on the configuration selected for the reactor.

Examples of bacteria in particular include those used as probiotics, including the species belonging to the *Bacillus, Lactobacillus, Bifidobacterium, Streptococcus* (which produce lactic fermentation), *Escherichia* or *Pseudomonas* genera.

Examples of yeasts include species from the *Saccharomyces* genus, in particular yeasts from the *Saccharomyces* genus genetically modified to block ethanol synthesis.

Natural or genetically modified microorganisms can be used, for example to consume carbohydrates, lipids or proteins by producing molecules less absorbable by the intestine or influencing the microbiota by modifying the physicochemical conditions.

Certain drugs or hormones (insulin, Glucagon-Like-Peptide 1 (GLP1), L-Dopa for example) are difficult to ingest, since it is difficult to protect them from the gastric pH and intestinal enzymes. Yet these molecules can be produced by bacteria or yeasts modified by genetic engineering, or in some cases by eukaryotic cells (animal or human Langerhans cells for insulin production, for example). The encapsulation of such microorganisms in the proposed reactor makes it possible to synthesize these molecules continuously in zones immediately capable of allowing them to be absorbed by the intestine. This is of interest is a new therapeutic approach in pathologies such as type I or type II diabetes, or Parkinson's disease.

According to the invention, the reactor may comprise microorganisms or eukaryotic cells capable of producing at least one molecule of therapeutic interest, in particular a polypeptide, for example L-dopa, GLP1 or insulin, in particular microorganisms genetically modified to produce at least one polypeptide, for example L-dopa, GLP1 or insulin.

It is also possible to use microorganisms, e.g., bacteria or yeasts, genetically modified to produce molecules capable of inhibiting or deactivating molecules involved in certain pathologies (vitamin K antagonists, anti-tau antibodies, precursor of the proteins that accumulate in Alzheimer's disease, etc.).

The microorganisms can be used to produce one or more essential amino acids. The nutritional needs for essential amino acids are significant in human health. For example, a tryptophan deficiency is known to cause depressive symptoms (serotonin pathway) or insomnia (melatonin). Microorganisms can be used to produce tryptophan, or other derivatives of the serotonin pathway.

In some physiopathological situations, some nonessential amino acids may become essential. As an example, in phenylketonurics, the tyrosine contribution is essential. Microorganisms can be used to produce tyrosine.

Microorganisms can be used that produce one or more of these essential amino acids.

When combating food shortages, it is also possible to consider giving the reactor the property of breaking down cellulose in order to provide an additional source of carbohydrates that are not naturally able to be assimilated by humans. In particular, the reactor may contain bacteria that secrete enzymes capable of breaking down cellulose.

It is also possible to use microorganisms, in particular genetically modified bacteria, to produce molecules capable of decreasing certain inflammatory intestinal reactions, in particular elafin, involved in gluten intolerance.

Examples of bacteria usable to produce a molecule of interest, by genetic modification (in particular by inserting a cassette or an expression system of said molecule), include *Lactobacillus salivarius*, or *Pseudomonas* sp., in particular *P. aeruginosa*, preferably in attenuated form. We may also cite the acceptable *E. coli* bacteria, such as the Nissle 1997 strain. The expression of the molecule of interest can be under the control of the gene coding for this molecule, for example via a signaling molecule able to be ingested by the patient.

It is also possible to use bacteria producing insulin or other molecules of the acetohexamide or acarbose type. Acarbose is a microbial pseudotetrasaccharide. At the brush border of the intestine, acarbose acts by competitive inhibition of the alpha-glucosidases. It thus decreases the breakdown of the carbohydrates (dioligo- and polysaccharides) into absorbable monosaccharides. Acarbose therefore decreases postprandial hyperglycemia, without causing hyperinsulinemia or weight change.

It is also possible to use bacteria producing the molecule in response to the presence of a starter contained in the alimentary bolus (type similar to lactose) or the like, for example an aspirin-inducible promoter, which imparts a property of control of the activity of the reactor.

The reactor may in particular be intended for a single use. The fastening element may also be intended for single use or may be reusable, which may be the case when it is provided to remove the reactor when the latter has reached its effectiveness deadline or expiration date, and to replace it with a new reactor or another type of reactor. The replacement can be done from the fastening element or more easily from a midpoint, for example on the swivel or another device separating the anchoring cord and the cord carrying the reactor.

The reactor according to the invention is used to contribute an active product to the inside of the intestine, in particular duodenum, small intestine or colon, and make it bioavailable. This use in particular seeks to generate, owing to this active product, a chemical reaction with one or more molecules present (in particular case of the reactor comprising one or more enzymes) or to produce (in particular case of the reactor comprising one or more microorganisms) one or more molecules that will have a chemical or biological function, or to modify the microbiota.

One use may in particular be the consumption of glucose present in the intestine, in particular in the duodenum and/or the jejunum, before it is absorbed. The reactor may then comprise one or more enzymes of the disaccharidases type (e.g., maltase, lactase, beta-fructosidase, alpha-glucosidase, beta-glucosidase, beta-galactosidase) and glucose oxidase and/or glucose dehydrogenase, or the like.

In this use, it is also possible to use a reactor comprising a microorganism capable of consuming the carbohydrates, lipids or proteins, associated with enzymes also able to break down these molecules, such as glucose oxidase and/or glucose dehydrogenase, one or a combination of microorganisms to consume the disaccharides and monosaccharides (in particular glucose), or disaccharidases associated with a microorganism capable of consuming simple sugars, in particular glucose.

In this use, the reactor may also comprise catalase and/or urease.

Other potential uses are conversion of proteins, lipids, or molecules such as oxygen, alcohol, lactose, gluten. In this case, the reactor comprises enzymes, in particular lactase or other galactosidases, acystine endoprotease or enzymes ALV001, ALV002 and ALV003.

Other potential uses are the production of biologically interesting molecules, in particular molecules sensitive to the passage in the digestive tract (digestive enzymes or pH, in particular), for example L-dopa, GLP1, insulin, or molecules capable of decreasing certain inflammatory intestinal reactions, in particular elafin, involved in gluten intolerance.

Other potential uses are the use of the reactor as a base for sowing or modifying the microbiota, by contributing microorganisms, in particular bacteria, and/or molecules that will influence the microbiota, for example by producing or consuming protons, ammonium ion, oxygen.

The invention also relates to the method of treating a mammal, human or animal, preferably human, in which a reactor according to the invention is implanted, and maintained there for a sufficient duration, for example several days, weeks, months or years. The reactor is positioned in the intestinal lumen, as indicated supra based on the embodiment. The method may in particular provide the fastening of an anchoring device in the wall of the stomach and the attachment of the reactor to this device, or the placement of a stent in the gastric antrum to which the reactor is connected or to which one connects the reactor, or the placement of an intestinal stent. The reactor can therefore assume one of the forms mentioned supra. This reactor, once placed, enables a chemical reaction with one or more molecules present (in particular case of the reactor comprising one or more enzymes) or the production (in particular case of the reactor comprising one or more microorganisms) of one or more molecules that will have a chemical or biological function, or microorganisms. The invention thus also relates to a method of treating a mammal, human or animal, preferably human, in which a device according to any one of the preceding claims is implanted in the digestive system, comprising a reactor bearing an active element, and an element fastening the reactor to an intestinal or gastric wall, the method comprising fastening the fastening element to the intestinal or gastric wall, and positioning the reactor in the intestinal lumen, owing to which the active element produces or can produce its biological or chemical effect.

Among the applications, in particular related to the metabolism of sugars, lipids or proteins, in particular glucose, examples include the treatment and/or prevention of obesity, type I or II diabetes, hypercholesterolemia. This method can therefore use a reactor comprising the combinations of enzymes and/or microorganisms that were presented supra.

The method according to the invention can be used in other applications, such as the treatment of food intolerances, Alzheimer's disease, Parkinson's disease, type I diabetes, etc.

The invention can therefore cover therapeutic methods and non-therapeutic methods, for example probiotic treatment, comfort treatment or food supplement-type treatment methods.

The invention will now be described in more detail using embodiments taken as non-limiting examples and in reference to the drawing, in which.

EXAMPLE 1

200 mg of chitosan is dissolved in 20 mL of acetic acid diluted at 0.5 vol % in water. A cross-linking agent, genipin at 0.0045 wt % by volume (g/100 mL) and cafeic acid are added to the initial mixture in a proportion of 0.0032 wt % by volume (g/100 mL) and the viscous chitosan solution after two hours of agitation. The genipin is solubilized beforehand in a solution of 12% dimethyl sulfoxide (DMSO) and 88% water ($H_2O$). The cafeic acid is solubilized beforehand at 4% in ethanol.

After 30 minutes of agitation, 3 g of this mixture is removed, which is spread on a smooth, non-adhesive substrate (diameter 28 cm), for example an antistatic polystyrene cup, and dried for 2 to 4 days at ambient temperature (a temperature comprised between 20 and 30° C. is appropriate). In another test, it is dried for three days at 25° C.

Flexible nanoporous membranes are thus obtained. Experiments done by the applicant have shown that this flexibility was related to the fact that the drying is done for a longer duration at ambient temperature. This feature is not obtained, for example, if drying temperatures above 40° C. are used. For a film thickness of about 7 to 15 µm, for example 10 µm, a porous membrane was obtained with mean pore diameters of about 1 to 10 nanometers. Preference will be given to conditions where this mean diameter is about 5 to 8 nm to allow the glucose to pass and to filter the largest compounds.

EXAMPLE 2

In a cylindrical tube (about 1 cm diameter and about 20 cm long) of cellulose acetate with a cutoff threshold at 5000 g·mole$^{-1}$ closed at one end, bacteria genetically modified to produce insulin is introduced up to a height of 4 cm in the tube. The other end of the tube is closed.

Then, the tube comprising the bacteria is flattened, and this flattened tube (thickness of about 1 to 2 mm) is placed on a first Dacron® ribbon (about 20 cm long and about 1.5 cm wide), then a second Dacron® ribbon is placed (about 20 cm long and about 1.5 cm wide) to form a device according to the invention in the form of a sandwich, having sewn the edges of the two ribbons together.

The assembly is fastened to a gastric clip using a Dacron® ribbon (about 15 cm long and about 1 cm wide). The clip is positioned endoscopically in the wall of the gastric antrum. Through the operating channel of the endoscope and with the clip, the ribbon is unwound and passed through the pylorus. The reactor containing the microorganisms is then positioned in the duodenum, after the ampulla of Vater, where the pancreatic and biliary ducts arrive.

EXAMPLE 3

A woven Dacron® ribbon is used to form a 50 cm×1 cm ribbon. At one of its ends, this ribbon is sutured to a gastric clip. The device is incubated for 48 hours in a culture medium of bacteria of the *Lactobacillus acidophilus* type. The clip is positioned endoscopically in the wall of the gastric antrum. Through the operating channel of the endoscope and with the clip, the ribbon is unwound and passed through the pylorus.

EXAMPLE 4

A Dacron® ribbon measuring 50 cm×1 cm is bent on a gastric clip. Added to the 200 mg of chitosan of example 1 is a mixture of 60 mg of glucose oxidase (100 International Units/mg), 60 mg of catalase (1000 International Units/mg) and 60 mg of beta-galactosidase (100 International Units/mg). After 30 min. of agitation, 3 g of the mixture is spread on one of the faces of the ribbon, over a length of 35 cm from the free end of the 50 cm×1 cm woven Dacron® ribbon. It is dried for 3 days at 25° C. The clip is positioned endoscopically in the wall of the gastric antrum. Through the operating channel of the endoscope and with the clip, the ribbon is unwound and passed through the pylorus. The reactor containing the microorganisms is then positioned in the duodenum, after the ampulla of Vater, where the pancreatic and biliary ducts arrive.

EXAMPLE 5

Figure 1:
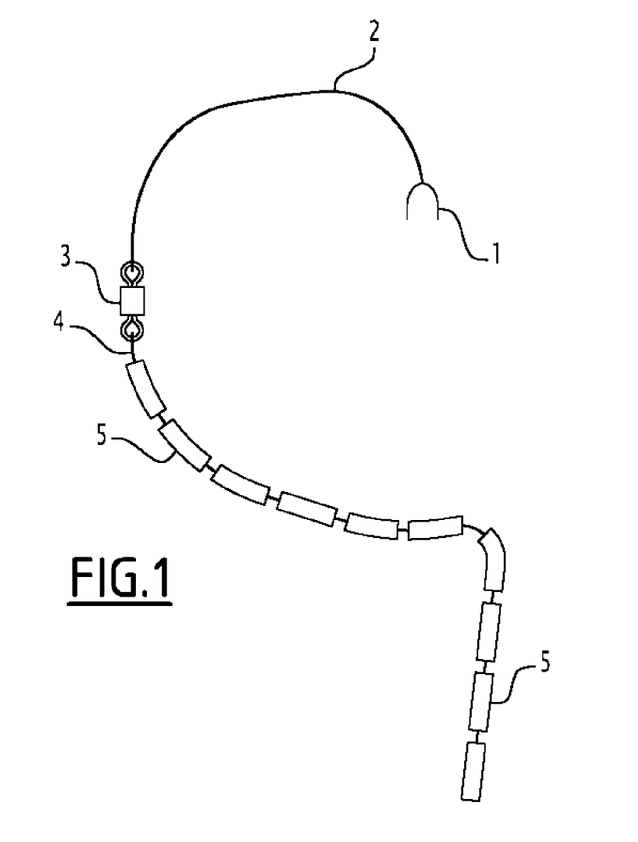
FIG. 1 is a diagrammatic illustration of a "segmented" device.
Figure 2:
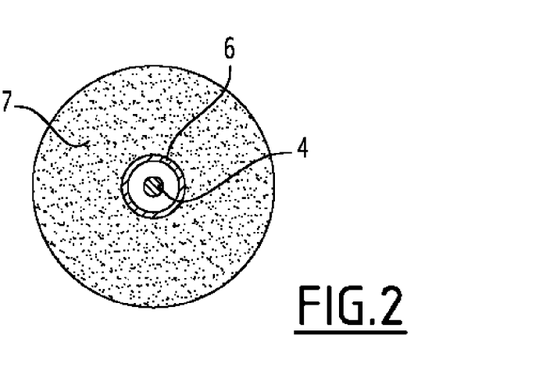
FIG. 2 shows the device of FIG. 1 in cross-section at a segment.

The device of FIG. 1 is made up of a stomach staple 1 fastened to one end of an anchoring rope or cord 2, which is fastened at its other end to one end of a swivel 3. The anchoring rope is a single-strand Teflon thread with a length of about 200 mm and a diameter of 1.0 mm. A second cord or rope 4 of single-strand Teflon has a length of about 300 mm and a diameter of 1.0 mm. It is fastened to the other end of the swivel 3, such that the ropes 2 and 4 and the swivel can rotate relative to one another. Mounted on the rope 4, over its entire length, are ten segments 5, called gyroplane segments because they can rotate around the rope 4. The structure will be better understood in reference to FIG. 2, which shows, in cross-section, a segment 5 and the rope 4 that it surrounds. Each segment is made up of a Teflon tube 6 with an outer diameter of 3 mm, an inner diameter of 1.6 mm and a length of 30 mm. Fastened on each tube 6 is a thick layer of expanded PVA 7, the outer diameter of the segment thus obtained being 6 mm. The expanded PVA can be the substrate for an active element, for example for development of a biofilm. The set of segments can thus be treated by the active element, or only some of them, depending on the area of the intestine in which one wishes to act. The mounting by freely rotating segments makes it possible to prevent the rope 4 from twisting under the influence of the forces that will be exerted on the device inside the intestine.

The length of the rope 4 will depend on the furthest area that must be reached in the intestine. A length of 150 mm can be used for the duodenal area. An additional length of 150 to 350 mm can be used for the jejunal area. The stomach staple 1 in turn is able to be fastened to the inner wall of the stomach, and its anchoring point as well as the length of the anchoring rope 2 allow the latter to extend into the vicinity of the pylorus.

In another embodiment, the device differs from that described above by the absence of the swivel 3, by a single tubular anchoring film (2+4) with an outer diameter of 2 mm, an inner diameter of 1 mm and a length of 500 mm, ten segments 5 with a length of 30 mm, and an inner diameter of 2.2 mm. In this embodiment, the tubular anchoring film allows the use of a coaxial rigid guidewire to place the device in the digestive tube. To that end, the rigid guidewire is placed beforehand from the oral opening, then the device is wound on this guidewire and pushed to the furthest distance that must be reached in the intestine.

EXAMPLE 6

Figure 3:
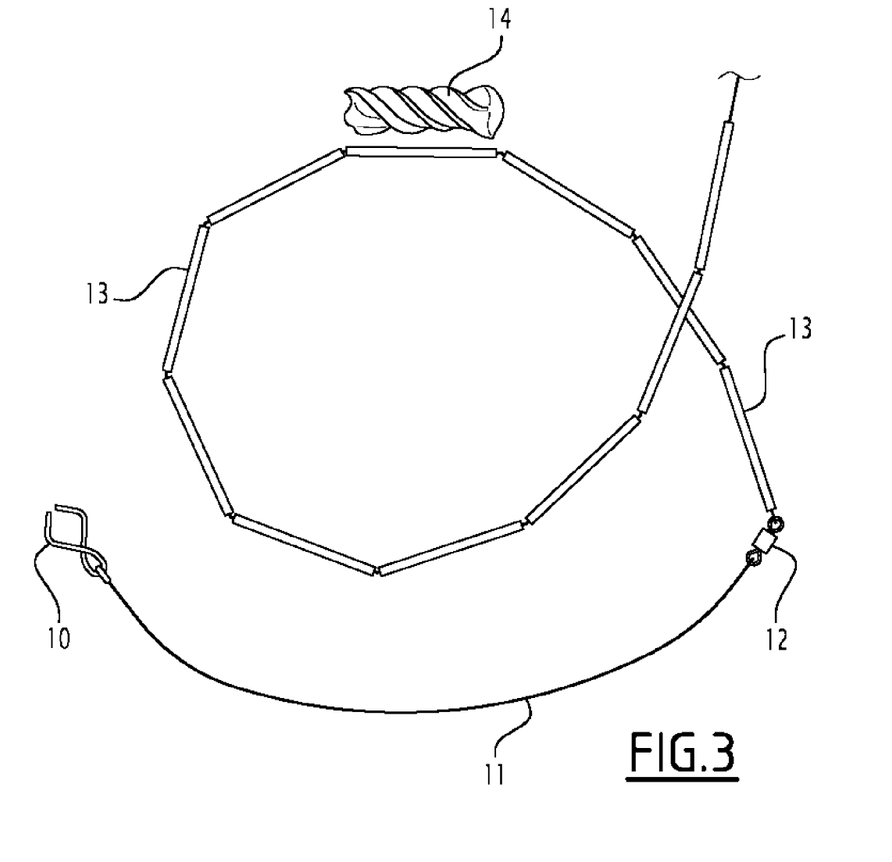
FIG. 3 is a schematic illustration of one embodiment of a segmented device according to another embodiment.
Figure 4:
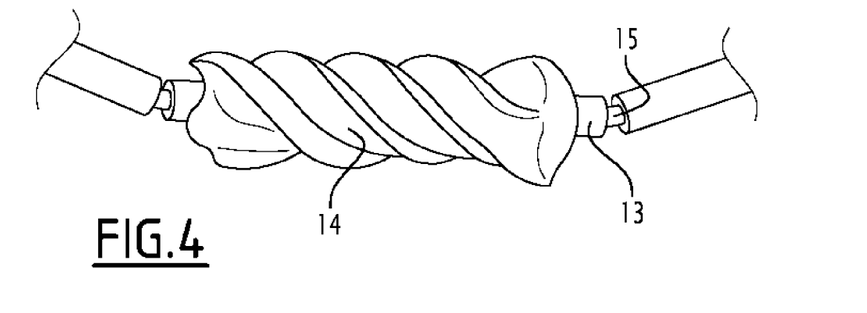
FIG. 4 is a schematic illustration of a segment of the device of FIG. 3.

This embodiment, shown in FIGS. 3 and 4, is fairly close to that of FIG. 1 regarding its general structure, with, in order, a stomach staple 10, a single-strand anchoring rope 11, a swivel 12, segments 13 mounted rotating on a single-strand nylon rope 15. Numerical reference 14 designates a spiral structure that is fastened on one of the segments 13. Like in example 5, the spiral structure, for example made from expanded PVA, can be the substrate for an active element, for example for development of a biofilm. One or several segments can be equipped with such a substrate, and the length of the rope 15 and the length and number of segments can easily be adjusted, to place the substrate(s) in the desired location in the intestine.

The invention claimed is:

1. A device implantable in an intestinal cavity, comprising a reactor, a cord, an active product, and a fastener for keeping the reactor in place in the intestinal cavity, wherein:
    said fastener is fastened to a fastening location on an intestinal or gastric wall;
    the cord connects the reactor to the fastener, and extends at least between the fastening location and the intestinal cavity, said cord having a solid section preventing the movement of the active product through the cord so that the cord remains free of the active product; and
    the active product is located in the interior or on the external surface of the reactor and comprises a chemical molecule that generates a chemical or biological reaction with one or more molecules present in an intestine, living microorganisms, or living eukaryotic cells.

2. The device according to claim 1, wherein the reactor comprises a semi-permeable membrane, a semi-permeable coating, or another semi-permeable material.

3. The device according to claim 1, wherein the reactor is fastened to the cord that secures it to the fastener.

4. The device according to claim 1, wherein the cord is surrounded by cylindrical segments.

5. The device according to claim 1, wherein the cord is mounted on a swivel.

6. The device according to claim 1, wherein the fastener is selected from the group consisting of a gastric clip, a pyloric stent, and an intestinal stent.

7. The device according to claim 1, wherein the reactor includes a semi-permeable or porous membrane, and defines a closed inner space.

8. The device according to claim 1, wherein the reactor defines an inner space containing at least one active element or product.

9. The device according to claim 1, wherein the reactor comprises a particulate or granular biocompatible material or a mass of biocompatible material.

10. The device according to claim 1, wherein the reactor contains a material selected from the group consisting of:
a disaccharidase;
bacteria breaking down glucose;
enzymes breaking down gluten;
a digestive enzyme inhibitor and/or an anorectic hormone;
microorganisms producing one or more essential amino acids;
microorganisms breaking down cellulose;
microorganisms producing dimethyl-butanol; and
bacteria producing insulin, acetohexamide, or acarbose.

11. The device according to claim 1, comprising genetically modified microorganisms that produce at least one molecule of therapeutic interest.

12. The device according to claim 1, comprising a microorganism genetically modified to produce a molecule, the production of this molecule that is induced by a signaling molecule ingested by the host.

13. The device according to claim 1, wherein the device generates at least one chemical reaction with one or more molecules present in the intestine or produces at least one biologically active molecule for the production of molecules of therapeutic interest or for the consumption of glucose present in the intestine before it is absorbed, the reactor comprising:
one or more enzymes of the disaccharidase type and glucose oxidase and/or a combination of glucose dehydrogenase, aldose reductase and NAD or NADP; or
microorganisms or eukaryotic cells capable of producing at least one molecule of therapeutic interest.

14. The device according to claim 1, wherein the reactor includes at least two faces on the surface of at least upon one of which a biofilm of microorganisms is formed, said biofilm allowing a sowing of microbiota.

15. The device according to claim 1, wherein the reactor includes one or more parts centered on the cord, said at least one or more parts having an essentially cylindrical shape or cross-section having at least one surface irregularity selected from the group consisting of:
a thickness variation in a longitudinal direction of the essentially cylindrical shape or cross-section;
a diameter variation along a diametrical direction of the essentially cylindrical shape or cross-section; and
a cavity set back from the essentially cylindrical shape or cross-section and having protuberances extending past the essentially cylindrical shape or cross-section.

16. The device according to claim 15, wherein an outer surface of the one or more parts having an essentially cylindrical shape or cross-section has a surface irregularity comprising a helical shape or a twist segment shape.

17. The device according to claim 1, wherein the length of the device is comprised between about 5 cm and about 150 cm.

18. A method of treating a mammal, human or animal, in which a device according to claim 1 is implanted, comprising fastening the fastener to the intestinal or gastric wall, and positioning the reactor in the intestinal lumen, owing to which the active element produces its biological or chemical effect.

19. The device according to claim 1, wherein the active product is selected from the group consisting of an enzyme and a microorganism, and said active product alters the physicochemical conditions in the intestinal cavity and modifies the intestinal microbiota.

20. The device according to claim 1, wherein the cord extends between the fastener and the reactor over a distance greater than the length of the reactor.

21. A device implantable in an intestinal cavity, comprising a reactor, a cord, an active product, and a fastener for keeping the reactor in place in the intestinal cavity, wherein:
said fastener is fastened to a fastening location on an intestinal or gastric wall;
the cord connects the reactor to the fastener, and extends at least between the fastening location and the intestinal cavity, said cord remaining free of the active product; and
the active product is located in the interior or on the external surface of the reactor and comprises a chemical molecule that generates a chemical with one or more molecules present in an intestine, or comprises a living microorganism or eukaryotic cell,
wherein when the active product is a chemical molecule, the chemical molecule is maintained in the reactor by a chemical matrix; and
wherein when the active product is a living microorganism or eukaryotic cell, said living microorganism or eukaryotic is immobilized on a face of the reactor in a biofilm.

* * * * *

UNITED STATES PATENT AND TRADEMARK OFFICE
CERTIFICATE OF CORRECTION

Page 1 of 1

PATENT NO.         : 10,960,191 B2
APPLICATION NO.    : 15/564105
DATED              : March 30, 2021
INVENTOR(S)        : Cinquin et al.

It is certified that error appears in the above-identified patent and that said Letters Patent is hereby corrected as shown below:

On the Title Page

Item (30):
Please change:
"Foreign Application Priority Data
April 3, 2015 (FR) ………………… 15 2927"
To:
"Foreign Application Priority Data
April 3, 2015 (FR) ………………… 1552927"

Signed and Sealed this
First Day of June, 2021

Drew Hirshfeld
*Performing the Functions and Duties of the*
*Under Secretary of Commerce for Intellectual Property and*
*Director of the United States Patent and Trademark Office*